(12) United States Patent
Layne

(10) Patent No.: US 6,558,414 B2
(45) Date of Patent: *May 6, 2003

(54) PARTIAL ENCAPSULATION OF STENTS USING STRIPS AND BANDS

(75) Inventor: Richard Layne, Phoenix, AZ (US)

(73) Assignee: Impra, Inc., Tempe, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/408,890

(22) Filed: Sep. 29, 1999

(65) Prior Publication Data

US 2001/0020181 A1 Sep. 6, 2001

Related U.S. Application Data

(60) Provisional application No. 60/118,269, filed on Feb. 2, 1999.

(51) Int. Cl.[7] .................................................. A61F 2/06
(52) U.S. Cl. ...................................... 623/1.13; 623/901
(58) Field of Search .............................. 623/1.15, 1.16, 623/1.13, 1.22, 1.28, 1.29, 1.49, 1.51, 1.27, 1.44, 901, 921

(56) References Cited

U.S. PATENT DOCUMENTS

| | | | |
|---|---|---|---|
| 4,324,574 A | * | 4/1982 | Fagan ........................... 55/487 |
| 4,776,337 A | | 10/1988 | Palmaz |
| 4,954,126 A | * | 9/1990 | Wallsten ...................... 623/1.1 |
| 5,078,736 A | | 1/1992 | Behl |
| 5,122,154 A | | 6/1992 | Rhodes |
| 5,123,917 A | | 6/1992 | Lee |
| 5,139,480 A | | 8/1992 | Hickle et al. |
| 5,158,548 A | | 10/1992 | Lau et al. |
| 5,192,311 A | * | 3/1993 | King et al. .................. 623/921 |
| 5,211,658 A | | 5/1993 | Clouse |
| 5,236,447 A | | 8/1993 | Kubo et al. |
| 5,242,399 A | | 9/1993 | Lau et al. |
| 5,258,027 A | | 11/1993 | Berghaus |
| 5,282,823 A | | 2/1994 | Schwartz et al. |
| 5,344,426 A | | 9/1994 | Lau et al. |
| 5,354,309 A | | 10/1994 | Schnepp-Pesch et al. |
| 5,383,928 A | | 1/1995 | Scott et al. |
| 5,384,019 A | * | 1/1995 | Keating et al. ............. 204/252 |
| 5,389,106 A | | 2/1995 | Tower |
| 5,395,390 A | | 3/1995 | Simon et al. |

(List continued on next page.)

FOREIGN PATENT DOCUMENTS

| | | |
|---|---|---|
| EP | 0 603 959 A1 | 6/1994 |
| EP | 0 792 627 | 9/1997 |
| EP | 0 893 108 | 1/1999 |
| FR | 2 671 482 A1 | 7/1992 |
| WO | WO 94/24961 | 11/1994 |
| WO | WO 97/21403 | 6/1997 |
| WO | WO 98/38947 | 9/1998 |
| WO | PCT/US 00/02886 | 7/2000 |

Primary Examiner—Bruce Snow
Assistant Examiner—Brian Pellegrino
(74) Attorney, Agent, or Firm—Morrison & Foerster

(57) ABSTRACT

Partially encapsulated stents are made using strips and bands of covering material. In one embodiment ringed stents are placed over an inner ePTFE tube (e.g., supported on a mandrel) and are covered by a series of longitudinal strips. A series of spaced apart ePTFE circumferential bands can then be placed over the top of the longitudinal strips and ringed stents; alternatively bands alone or strips alone may be employed. All of the components of the structure are then laminated to the inner ePTFE tube to capture the stent. By selecting the size and position of the ePTFE bands, it is possible to leave critical parts of the stent unencapsulated to facilitate flexibility and expansion. The longitudinal strips can be woven about the stent and later laminated into position to provide an anti-compression function as well as overall structural stability. Although a single stent can be used, these approaches lend themselves to use of a plurality of individual ring stents spaced apart along the inner ePTFE tube.

7 Claims, 2 Drawing Sheets

U.S. PATENT DOCUMENTS

| | | |
|---|---|---|
| 5,421,955 A | 6/1995 | Lau et al. |
| 5,437,083 A | 8/1995 | Williams et al. |
| 5,443,496 A | 8/1995 | Schwartz et al. |
| 5,458,615 A | 10/1995 | Klemm et al. |
| 5,474,563 A | 12/1995 | Myler et al. |
| 5,507,767 A | 4/1996 | Maeda et al. |
| 5,507,768 A | 4/1996 | Lau et al. |
| 5,514,154 A | 5/1996 | Lau et al. |
| 5,522,881 A * | 6/1996 | Lentz ........................ 623/1.13 |
| 5,527,353 A | 6/1996 | Schmitt |
| 5,546,646 A | 8/1996 | Williams et al. |
| 5,549,663 A | 8/1996 | Cottone, Jr. |
| 5,554,181 A | 9/1996 | Das |
| 5,569,295 A | 10/1996 | Lam |
| 5,591,223 A | 1/1997 | Lock et al. |
| 5,593,417 A | 1/1997 | Rhodes |
| 5,603,721 A | 2/1997 | Lau et al. |
| 5,632,840 A | 5/1997 | Campbell |
| 5,645,559 A | 7/1997 | Hachtman et al. |
| 5,649,950 A | 7/1997 | Bourne et al. |
| 5,649,977 A | 7/1997 | Campbell |
| 5,653,727 A | 8/1997 | Wiktor |
| 5,653,747 A | 8/1997 | Dereume |
| 5,667,523 A | 9/1997 | Bynon et al. |
| 5,681,345 A * | 10/1997 | Eutener ....................... 606/198 |
| 5,693,085 A | 12/1997 | Buirge et al. |
| 5,700,286 A * | 12/1997 | Tartaglia et al. ........... 623/1.15 |
| 5,713,949 A | 2/1998 | Jayaraman |
| 5,718,973 A | 2/1998 | Lewis et al. |
| 5,723,003 A | 3/1998 | Winston et al. |
| 5,728,158 A | 3/1998 | Lau et al. |
| 5,735,892 A | 4/1998 | Myers et al. |
| 5,735,893 A | 4/1998 | Lau et al. |
| 5,738,674 A | 4/1998 | Williams et al. |
| 5,749,880 A * | 5/1998 | Banas et al. ................. 606/198 |
| 5,755,770 A | 5/1998 | Ravencroft |
| 5,755,774 A | 5/1998 | Pinchuk |
| 5,766,238 A | 6/1998 | Lau et al. |
| 5,769,884 A | 6/1998 | Solovay |
| 5,810,870 A | 9/1998 | Myers et al. |
| 5,824,037 A | 10/1998 | Fogarty et al. |
| 5,824,043 A | 10/1998 | Cottone, Jr. |
| 5,824,046 A | 10/1998 | Smith et al. |
| 5,824,054 A | 10/1998 | Khosravi et al. |
| 5,843,161 A | 12/1998 | Solovay |
| 5,843,166 A | 12/1998 | Lentz et al. |
| 5,849,037 A | 12/1998 | Frid |
| 5,851,232 A | 12/1998 | Lois |
| 5,876,448 A | 3/1999 | Thompson et al. |
| 6,004,348 A | 12/1999 | Banas et al. |
| 6,015,431 A * | 1/2000 | Thornton et al. .......... 623/23.7 |
| 6,042,605 A * | 3/2000 | Martin et al. ................. 623/1.5 |

* cited by examiner

PARTIAL ENCAPSULATION OF STENTS USING STRIPS AND BANDS

This application claims the benefit of U.S. Provisional Application No. 60/118,269, filed Feb. 2, 1999.

BACKGROUND OF THE INVENTION

1. Field of the Invention

The present invention relates generally to the field of medical devices, and more particularly, to the encapsulation of stents.

2. Description of Related Art

Stents and similar endoluminal devices are currently used by medical practitioners to treat portions of the vascular system that become so narrowed (stenosed) that blood flow is restricted. Such narrowing (stenosis) occurs, for example, as a result of the disease process known as arteriosclerosis. Angioplasty of a coronary artery to correct arteriosclerosis may stimulate excess tissue proliferation, which then blocks (restenosis) the newly reopened vessel. While stents are most often used to "prop open" blood vessels, they can also be used to reinforce collapsed or narrowed tubular structures in the respiratory system, the reproductive system, biliary ducts or any other tubular body structure. However, stents are generally mesh-like so that endothelial and other cells can grow through the openings resulting in restenosis of the vessel.

Polytetrafluoroethylene (PTFE) has proven unusually advantageous as a material from which to fabricate blood vessel grafts or prostheses, tubular structures that can be used to replace damaged or diseased vessels. This is partially because PTFE is extremely biocompatible causing little or no immunogenic reaction when placed within the human body. This is also because in its preferred form, expanded PTFE (ePTFE), the material is light and porous and is readily colonized by living cells so that it becomes a permanent part of the body. The process of making ePTFE of vascular graft grade is well known to one of ordinary skill in the art. Suffice it to say that the critical step in this process is the expansion of PTFE into ePTFE. This expansion represents a controlled longitudinal stretching in which the PTFE is stretched to several hundred percent of its original length.

If stents could be enclosed in ePTFE, cellular infiltration could be prevented, hopefully preventing restenosis. Early attempts to produce a stent enshrouded with ePTFE focused around use of adhesives or physical attachment such as suturing. However, such methods are far from ideal and suturing, in particular, is very labor intensive. More recently methods have been developed for encapsulating a stent between two tubular ePTFE members whereby the ePTFE of one-member touches and bonds with the ePTFE of the other member through the mesh opening in the stent. Unfortunately, such a monolithically encapsulated stent tends to be rather inflexible. In particular, radial expansion of the stent may stress and tear the ePTFE cover. Therefore, there is a need for a stent that is encapsulated to provide a smooth inner surface for the flow of blood and yet still allows expansion of the stent without tearing or delaminating, providing a relatively flexible device.

SUMMARY OF THE INVENTION

The present invention is directed to partially encapsulating stents wherein flexibility of the stent is retained, despite encapsulation. This can be done by placing a plurality of longitudinal strips over the stent or series of stents rings made of ePTFE and/or placing a plurality of circumferential ePTFE bands over the stent(s).

It is an object of this invention to provide a stent device that has improved flexibility, yet maintains its shape upon expanding or contracting.

It is also an object of this invention to provide a stent encapsulated to prevent cellular infiltration, wherein portions of the stent can move during radial expansion without stressing or tearing the encapsulating material.

These and additional objects are accomplished by embedding or encapsulating only a portion of the stent. In this way, the unencapsulated portion of the stent is free to move during expansion without compromising the ePTFE covering. The most straightforward way of achieving partial encapsulation is to place the stent(s) over an inner ePTFE tubular member (e.g., supported on a mandrel) and then to cover the outer surface of the stent(s) with a series of spaced apart longitudinal ePTFE strips, which are then laminated to the inner ePTFE to capture the stent. These strips (e.g., cut from an extension of the inner ePTFE tube) can be woven about the stent(s) and later laminated into position to provide an anti-compression function as well as overall structural stability. Beside strips of ePTFE it is also possible to use circumferential ePTFE bands to further or alternatively capture the stent(s). By selecting the size and position of the bands it is possible to leave critical parts of the stent unencapsulated to facilitate flexibility and expansion. Although a single stent can be used, these approaches lend themselves to use of a plurality of individual ring stents spaced apart along the inner ePTFE tube.

In the present invention, individual ring stents are partially encapsulated using the procedure outlined above. Preferably, ring stents of zigzag sinusoidal structure are placed "in phase" on the outside surface of a tubular ePTFE graft supported by a mandrel. Separate bands of ePTFE are placed over the stent rings, so that some portion of the stent rings is covered. In addition, longitudinal strips of ePTFE can be woven (e.g., over and under) about the ring stents, either before or after the bands are applied. The resulting structure is then subjected to heat and pressure so that the regions of ePTFE become laminated or fused together. In addition, the ends of the stent can be completely encapsulated, by known methods, to stabilize the overall structure.

A more complete understanding of the partial encapsulation of stents will be afforded to those skilled in the art, as well as a realization of additional advantages and objects thereof, by a consideration of the following detailed description of the preferred embodiment. Reference will be made to the appended sheets of drawings, which will first be described briefly.

DETAILED DESCRIPTION OF THE PREFERRED EMBODIMENT

The present invention satisfies the need for an encapsulated stent device to prevent restenosis that is flexible upon expansion and contraction so that the general structural form is retained. This is accomplished by partially encapsulating a stent or stent rings using connected strips and bands of ePTFE.

Figure 1:
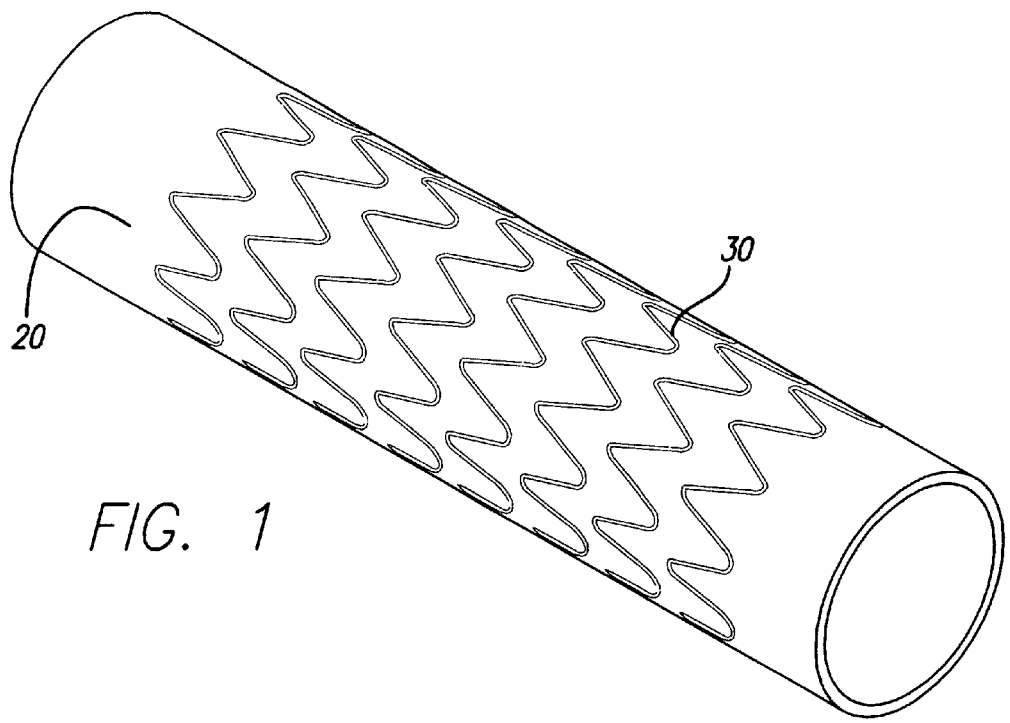
FIG. 1 is a perspective view of a tubular ePTFE member with individual ring stents arranged over the outside.
Figure 2:
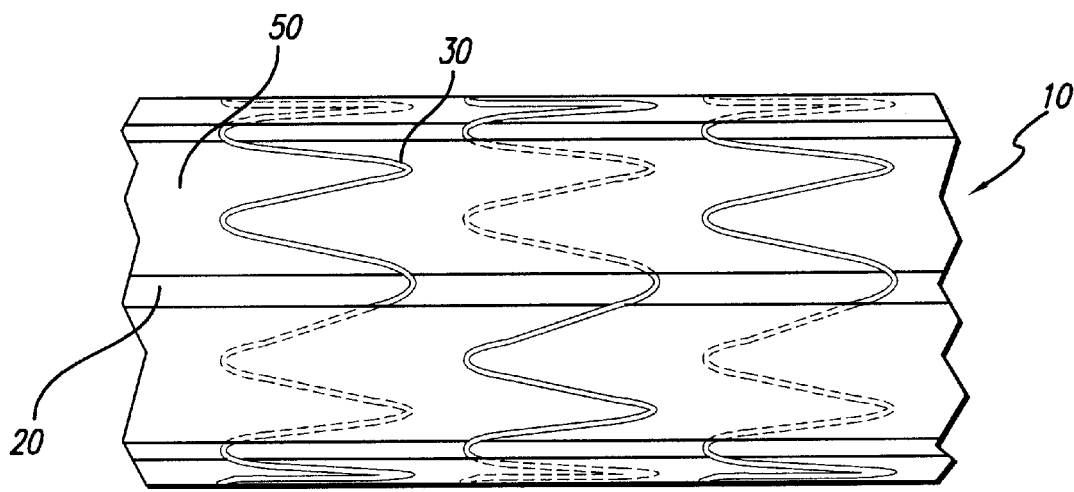
FIG. 2 is a sectional view of the device in FIG. 1 with longitudinal strips of ePTFE interwoven between the ring stents.

Referring now to the drawings, in which like reference numbers represent similar or identical structures throughout, FIG. 1 illustrates an initial step in constructing the partially encapsulated stent of the present invention. A tubular ePTFE graft 20 is placed over a mandrel for the assembly of a device 10 (FIG. 2). A stent is then placed over the graft 20. In the preferred embodiment, as shown in FIG. 1, a series of zigzag sinusoidal ring stents 30 are placed over the outer surface of the graft 20. These ring stents 30 can be made of any material, but a preferred material is metal. The zigzag ring stents 30 may be assembled "in phase" with each adjacent ring stent having peaks and valleys aligned. Alternatively, the individual stents 30 can be "out of phase" to different degrees. It will be apparent that the phase relation of adjacent stents 30 will alter the lateral flexibility as well as the longitudinal compressibility of the structure. The phase relationship can be varied along the length of the device 10, thereby altering the physical properties in different portions of the device 10. Having individual ring stents 30, as opposed to a single tubular stent, provides the advantage that the periodicity, or the number and precise shape of the zigzags per ring, can readily be varied along the length of the graft to influence flexibility and stability properties of the structure. Also, spacing of the individual stents (number of stents per unit length) as well as the phase relationship of stent to stent can be varied to produce stent grafts with desired properties. By placing the ring stents 30 over the outer surface of the tubular ePTFE graft 20, the resulting structure has an inner (luminal) surface that is completely smooth to facilitate the flow of blood. However, there may be instances where the ring stents 30 or other tubular stents are advantageously placed on the inner graft surface or on both the inner and outer surfaces, as one of ordinary skill in the art will readily appreciate.

A preferred embodiment of the present invention can be seen in FIG. 2. The ring stents 30 are longitudinally stabilized by strips of ePTFE 50 that are woven between the adjacent ring stents 30 and the underlying graft 20. These anti-compression strips 50 are woven so that a given strip 50 passes over one ring stent 30 and under an adjacent stent 30 and so on. Just as in actual weaving, a complex pattern can be developed with a given strip 50 passing over several stents 30 before passing under one or more stents 30. Thus a "twill" or other weave can be implemented with significant effects on flexibility and similar physical properties. This woven pattern can vary from strip to strip so that each ring stent 30 is held down by at least one strip 50.

Figure 4:
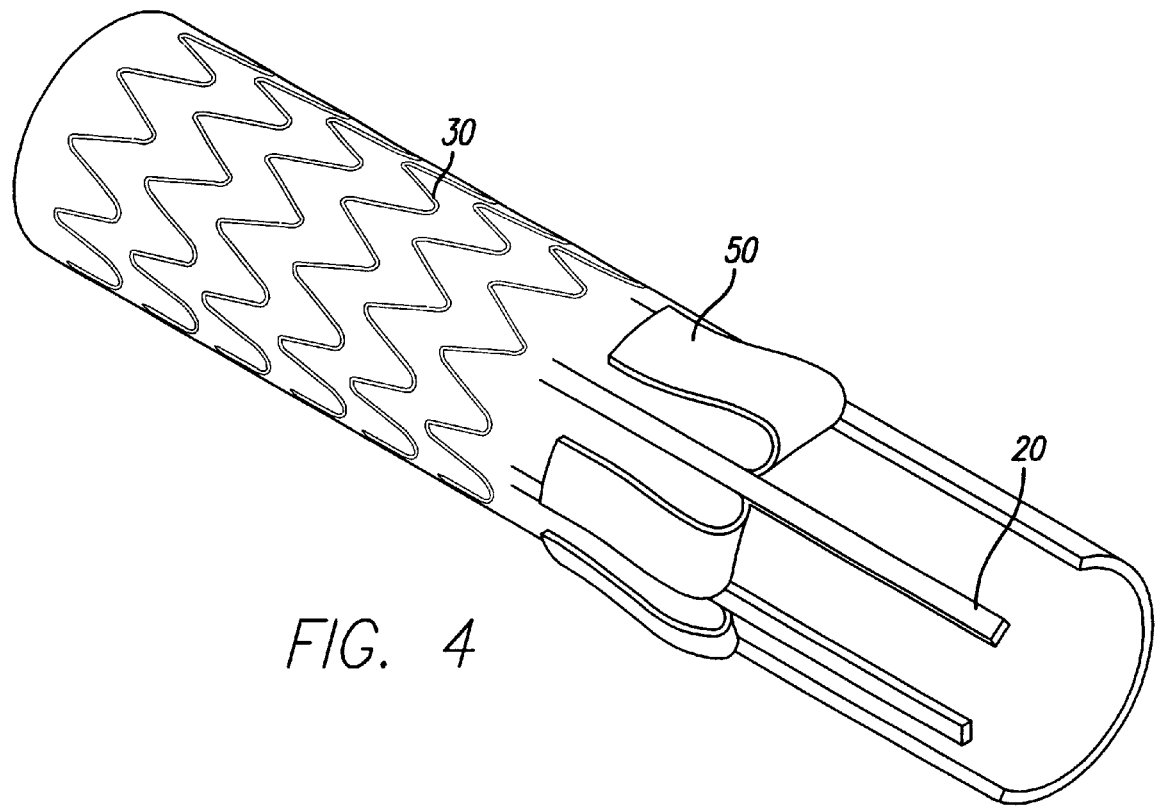
FIG. 4 is a perspective view of a tubular ePTFE member of the present invention, showing one end divided into a section of longitudinal strips and folded back over the remaining ePTFE member and ring stents disposed thereon.

One way of achieving this effect is to pull a tubular graft member onto a mandrel, leaving a terminal overhang at least as long as the portion on the mandrel. This overhang is then slit into a number of strips 50 as shown in FIG. 4. The strips 50 are folded over and laid along the mandrel. Two opposite strips are lifted while a first ring stent is slid over the mandrel (and two of the strips) and brought to rest at the end of the mandrel nearest the origin of the strips. Then the previously lifted strips are laid along the mandrel and the other two strips are lifted. A second ring stent is slid onto the mandrel over the strips that were lifted for the first ring stent. This weaving process is continued until a full compliment of stents is on the mandrel. At this time, the resulting structure is subjected to heat and pressure to laminate the woven strips to the underlying ePTFE graft. Obviously, any number of strips can be employed and the pattern of lifted strips can be varied to create any of a number of woven patterns. Alternatively, each adjacent strip could alternate between going over all of the stents and under all of the stents. FIG. 4 shows the beginning of a weaving process, similar to that explained above, wherein adjacent strips are alternatingly woven over and under each successive ring stent.

Figure 3:
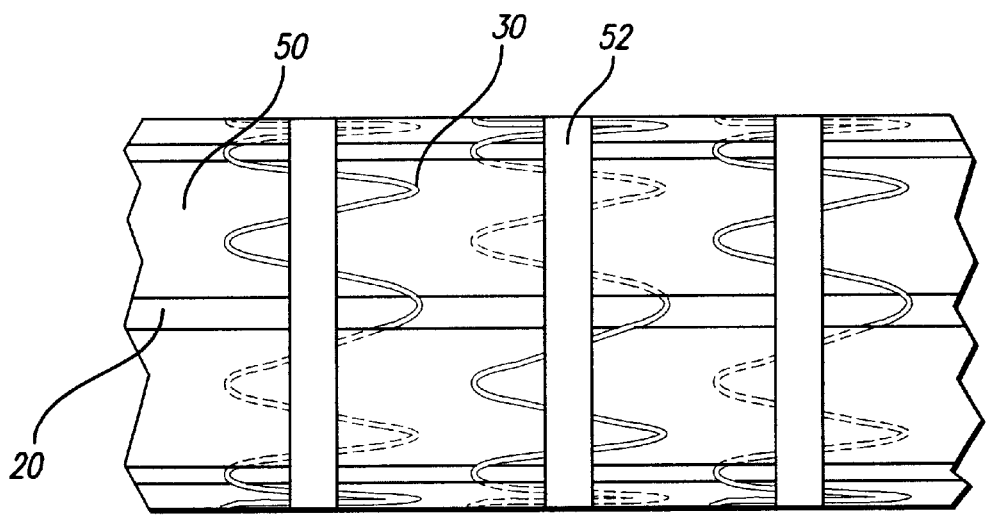
FIG. 3 is a sectional view of the device in FIG. 2 with circumferential strips of ePTFE placed over the top.

In FIG. 3, a second embodiment is illustrated, utilizing longitudinal ePTFE strips 50 for stabilizing the structure 60 and circumferential ePTFE bands 52 for holding the ring stents 30 in place. In addition, an end ePTFE ring is used to fully encapsulate each longitudinal end of structure 60 for further stability. It should be appreciated that the bands of ePTFE 52 that are placed over the top of the ring stents 30 can encompass many different designs. The spaces between the bands of ePTFE 52 can be altered to control the degree of flexibility and stability desired. In the preferred embodiment shown in FIG. 3, the bands 52, placed over the center portion of each ring stent 30 are intended to cover the circumference of each ring stent 30, leaving the ends of the zigzags uncovered. By circumferentially covering a portion of each ring stent 30, the maximum amount of lateral flexibility is provided. However, circumferentially covering the individual ring stents 30 without any longitudinal support would result in a structure with little longitudinal strength and stability that would be prone to "telescoping". Thus, the longitudinal strips 50 that are incorporated under the bands of ePTFE 52 are important, making the preferred design in FIG. 3 optimal. The longitudinal strips 50 are completely laminated to the underlying graft 20 and act as "anti-compression" devices by resisting the shortening of the structure 60. The width of the bands 52 and the anti-compression strips 50 control longitudinal strength and stability versus lateral flexibility. By adjusting these parameters, grafts can be made more or less flexible with greater or lesser anti-compression strength. In a preferred embodiment, four longitudinal strips 50 are used and the ends of the structure 60 are completely encapsulated for greater stability. Of course, a larger number of anti-compression strips 50 can be employed. Also, the strips 50 may themselves zigzag or may be helically arranged. Each different structure has different properties. Similarly, the bands 52 can have different forms and may be undulating (sinusoidal) in form. In fact, there is nothing to preclude a structure including a complex pattern where individual bands 52 and strips 50 are difficult to discern.

After the strips 50 and/or bands 52 are configured in the desired pattern onto each of the structures 10 and 60, the structures are exposed to heat and pressure, such as that caused by wrapping with PTFE tape, thereby causing the ePTFE regions of the strips 50 and/or bands 52 to fuse or laminate to the tubular graft 20. Of course, depending on the desired properties the numbers of strip 50 and bands 52 may be varied greatly. The inventor specifically contemplates devices with no bands 52 or devices with no strips 50.

Having thus described a preferred embodiment of the partial encapsulation of stents using strips and bands, it will be apparent by those skilled in the art how certain advantages of the present invention have been achieved. It should also be appreciated that various modifications, adaptations, and alternative embodiments thereof may be made within the scope and spirit of the present invention. For example, zigzag stent rings have been illustrated, but it should be apparent that the inventive concepts described above would be equally applicable to sinusoidal and other stent designs. Moreover, the words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result. The described embodiments are to be considered illustrative rather than restrictive. The invention is further defined by the following claims.

I claim:

1. A vascular graft, comprising:
   an expanded polytetrafluoroethylene tube including a first section and a second section, wherein the first and second sections share a common surface, the second section comprising a plurality of strips extending from the first section, being integral therewith; and
   a support layer comprising a plurality of ringed stents placed around said first section, wherein said strips are folded back and are alternatingly woven over and under each successive ringed stent.

2. The vascular graft of claim 1, further comprising a plurality of independent circumferential bands disposed over at least a portion of the support layer.

3. The vascular graft of claim 1, wherein said ringed stents are formed in a zigzag pattern of alternating peaks and valleys.

4. The vascular graft of claim 3, wherein said zigzag ringed stents are placed around said first section with the alternating peaks and valleys in phase.

5. The vascular graft of claim 1, wherein said stent is made of metal.

6. The vascular graft of claim 1, wherein a first longitudinal strip is woven over a first ringed stent, wherein a second longitudinal strip, adjacent to said first longitudinal strip, is woven under a first ringed stent, and wherein each successive adjacent odd numbered longitudinal strip is woven over a first ringed stent and each successive adjacent even numbered longitudinal strip is woven under a first ringed stent.

7. The vascular graft of claim 1, wherein both a proximal and a distal end of said vascular graft are encapsulated.

* * * * *